United States Patent
Bose et al.

(10) Patent No.: US 9,012,669 B2
(45) Date of Patent: Apr. 21, 2015

(54) EFFICIENT PROCESSES FOR LARGE SCALE PREPARATION OF PHOSPHAPLATINS ANTITUMOR AGENTS

(71) Applicants: Rathindra N. Bose, Athens, OH (US); Shadi Moghaddas, Manvel, TX (US); Homa Dezvareh, Pearland, TX (US)

(72) Inventors: Rathindra N. Bose, Athens, OH (US); Shadi Moghaddas, Manvel, TX (US); Homa Dezvareh, Pearland, TX (US)

(73) Assignee: The University of Houston System, Houston, TX (US)

( * ) Notice: Subject to any disclaimer, the term of this patent is extended or adjusted under 35 U.S.C. 154(b) by 166 days.

(21) Appl. No.: 13/646,152

(22) Filed: Oct. 5, 2012

(65) Prior Publication Data
US 2013/0165680 A1 Jun. 27, 2013

Related U.S. Application Data

(60) Provisional application No. 61/543,540, filed on Oct. 5, 2011.

(51) Int. Cl.
C07F 15/00 (2006.01)
C07F 19/00 (2006.01)

(52) U.S. Cl.
CPC ........... *C07F 19/005* (2013.01); *C07F 15/0093* (2013.01)

(58) Field of Classification Search
CPC .................................................. C07F 15/0093
USPC ........................................................ 556/17
See application file for complete search history.

(56) References Cited

U.S. PATENT DOCUMENTS

| 7,700,649 B2 | 4/2010 | Bose | |
| 8,034,964 B2 * | 10/2011 | Bose | ............................... 556/17 |
| 2009/0042838 A1 | 2/2009 | Bose | |
| 2010/0233293 A1 | 9/2010 | Bose | |
| 2011/0092465 A1 * | 4/2011 | Doyle | ........................... 514/106 |
| 2013/0064902 A1 | 3/2013 | Bose | |

FOREIGN PATENT DOCUMENTS

WO  2009021081 A2  2/2009

OTHER PUBLICATIONS

Bose et al. "Non-DNA-binding platinum anticancer agents: Cytotoxic activities of platinum-phosphato complexes towards human ovarian cancer cells", PNAS, Nov. 25, 2008.
U.S. Appl. No. 13/701,313, filed Mar. 14, 2013, Bose.
Mishur, Robert J. et al, Synthesis, X-ray Crystallographic and NMR Characterizations of Platinum (II) and Platinum (IV) Pyrophosphato Complexes, Inroganic Chemistry, 2008, 47, 7972-7982.

(Continued)

*Primary Examiner* — Porfirio Nazario Gonzalez
(74) *Attorney, Agent, or Firm* — Winstead PC

(57) ABSTRACT

An efficient process for synthesizing phosphaplatins in large quantities is disclosed by adding platinum complex to a concentrated pyrophosphate solution at pH from between about 6.0 to 8.5. After stirring, the temperature and pH are lowered to precipitate out desired phosphaplatins. Particularly, the disclosed processes reduce the need to use large volumes of starting materials, and shorten the reaction time. In addition, disclosed is a process for recycling un-reacted materials from a first phosphaplatins synthesis.

19 Claims, 7 Drawing Sheets

(56) References Cited

OTHER PUBLICATIONS

Bose, Rithindra H. el al, "Non-DNA-binding platinum anticancer agents: Cytotoxic activities of platinum-phosphato complexes towards human ovarian cancer cells", PNAS, Nov. 25, 2008, vol. 105, No. 47, pp. 18314-18319.
Mishur, Robert J. et al, "Synthesis, X-ray Crystallographic and NMR Characterizations of Platinum (II) and Platinum (IV) Pyrophosphato Complexes", Inorganic Chemistry, 2008, 47, 7972-7982.
Bose, Rathindra N. et al, "Non-DNA-binding platinum anticancer agents: Cytotoxic activities of platinum-phosphato complexes towards human ovarian cancer cells", PNAS, Nov. 25, 2008, vol. 105, No. 47, pp. 18314-18319.
Moghaddas, Shadi et al, Superior Efficacy of Phosphoplatins: Novel Non-DNA-Binding Platinum Drugs for Human Ovarian Cancer, FASEB J. 2010, 24:527.2.

* cited by examiner

EFFICIENT PROCESSES FOR LARGE SCALE PREPARATION OF PHOSPHAPLATINS ANTITUMOR AGENTS

CROSS-REFERENCES TO RELATED APPLICATIONS

This application claims priority to U.S. provisional application No. 61/543,540, filed on Oct. 5, 2011, which is herein incorporated by reference in its entirety.

GOVERNMENTAL SPONSORSHIP

Not applicable.

FIELD OF THE INVENTION

The invention relates to efficient synthetic and reaction management processes for the production of phosphaplatin antitumor agents that can be applied to large scale industrial production.

BACKGROUND OF THE INVENTION

Phosphaplatins are pyrophosphate coordinated platinum (II) and platinum(IV) complexes containing inert amine ligands (R. J. Mishur, et al., Synthesis and X-ray crystallographic Characterization of Monomeric Platinum(II)- and Platinum(IV)-Pyrophosphato Complexes, *Inorg. Chem.*, 2008, 47, 7972-7982). These compounds show excellent antitumor activities against a variety of human cancers as demonstrated by both in vitro (R. N. Bose, et al., Non-DNA Binding Platinum Anticancer Agents: Remarkable Cytotoxic Activities of Platinum-phosphato Complexes Towards Human Ovarian Cancer Cells, *Proc. Natl. Acad. Sci.*, 2008, 105, 18314-18419) and in vivo experiments using Scid and Nude mice (S. Moghaddas, et al., Superior Efficacy of Phosphaplatins: Novel Non-DNA-Binding Platinum Drugs for Human Ovarian Cancer, *FASEB J.*, 2010, 24:527; S. Moghaddas, et al., Phosphaplatins, Next Generation Platinum Antitumor Agents: A Paradigm Shift in Designing and Defining Molecular Targets, *Inorg. Chim. Acta.*, DOI, 10.1016/j.ica.2012.05.040, ISSN 0020-1693). Moreover, these compounds show reduced toxicity compared to other platinum chemotherapeutics.

Current methods for synthesizing phosphoplatins, as described in published articles (R. J. Mishur, et al., Synthesis and X-ray crystallographic Characterization of Monomeric Platinum(II)- and Platinum(IV)-Pyrophosphato Complexes, *Inorg. Chem.*, 2008, 47, 7972-7982) and in issued and pending patent applications (U.S. Pat. No. 7,700,649; U.S. Pat. No. 8,034,964; WO2011/053365), the contents of which are herein incorporated by reference in their entirety, require large reaction volumes to produce small quantities of products. These established methods are limited by the solubility of the starting platinum reactants. For example, to produce (trans-1,2-Cyclohexanediamine) (dihydrogen pyrophosphato) platinum(II) complex in 50 to 70 mg quantities, a starting volume of aqueous solution of 250 mL is required. Furthermore, to precipitate the same quantity of compound, the original volume needs to be reduced from 250 mL to 5 mL. Therefore, to scale up the synthesis to one kilogram of the compound, five thousand liters of starting volume is needed. Also, the cost for reducing such a large volume from 5000 L to 100 L to precipitate the product is significant. Secondly, the reported methodology does not recycle for use the un-reacted platinum starting reagent and excess pyrophosphate. Finally, the established large-volume synthesis requires a long reaction time, usually 12 to 24 hr for a batch of 50 to 70 mg materials. Therefore, there is a need in the art for a process that synthesizes large quantities of phosphaplatins for treating cancer patients and other applications where significant quantities of compounds will be required, and that optimally uses the reactants for maximum yield, and reduces reaction time.

SUMMARY OF THE INVENTION

In one embodiment of the invention, a process is disclosed for synthesizing phosphaplatins on a large scale. The process eliminates the need to use large volumes of starting materials by increasing the solubility of those starting materials in a low volume reaction mixture. Furthermore, the process eliminates the need to use concentration procedures during precipitation of the desired phosphaplatins. Finally, the process significantly reduces the reaction time.

In one embodiment, platinum complex is slowly added to a reaction mixture containing concentrated pyrophosphate at a pH between about 6.0 to 8.5. After stirring, the temperature and pH are lowered to precipitate our desired phosphaplatins.

In another embodiment of the invention, a process is disclosed for recycling un-reacted platinum complex and pyrophosphate after a first synthesis of phosphaplatins. After the first synthesis, waste product is filtered from the reaction mixture and appropriate starting materials are added to yield further phosphaplatins.

BRIEF DESCRIPTION OF THE DRAWINGS

The foregoing summary, as well as the following detailed description, will be better understood when read in conjunction with the appended drawings. For the purpose of illustration, there is shown in the drawings certain embodiments of the present disclosure. It should be understood, however, that the invention is not limited to the precise arrangements and instrumentalities shown.

DETAILED DESCRIPTION OF THE INVENTION

Figure 1:
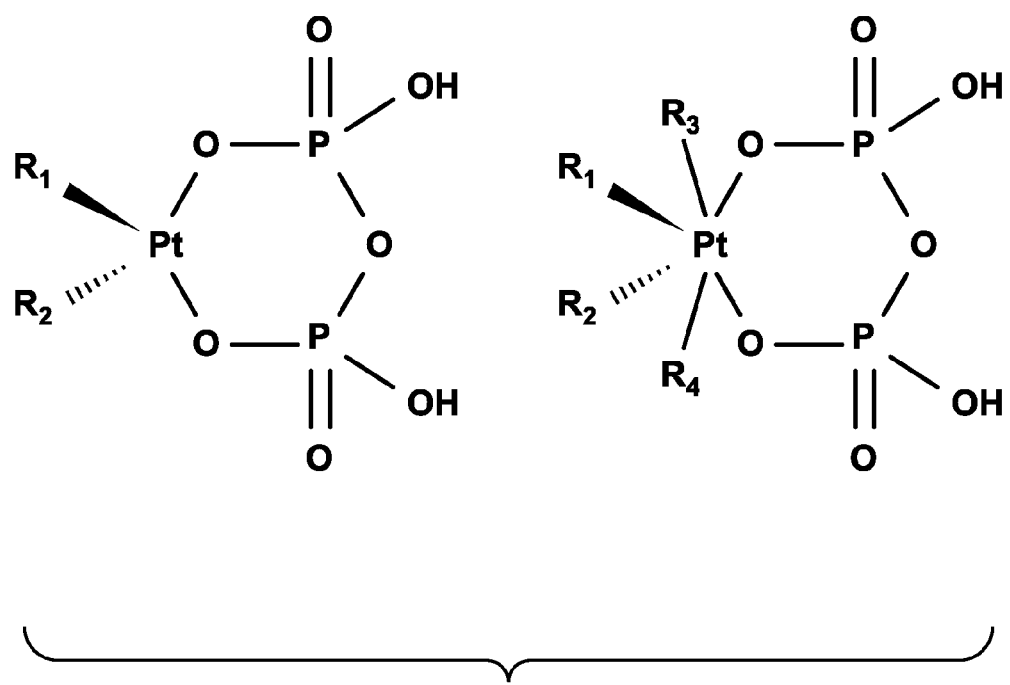
FIG. 1. Shows the general formula (I) of phosphaplatin antitumor agents where R1 and R2 are amine ligands, and R3 and R4 are either amine or other monodentate ligands.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It should be understood that any one of the features of the invention may be used separately or in combination with other features. Other systems, methods, features, and advantages of the invention will be or become apparent to one with skill in the art upon examination of the drawings and the detailed description. It is intended that all such additional systems, methods, features, and advantages be included within this description, be within the scope of the present invention, and be protected by the accompanying claims.

Figure 2:
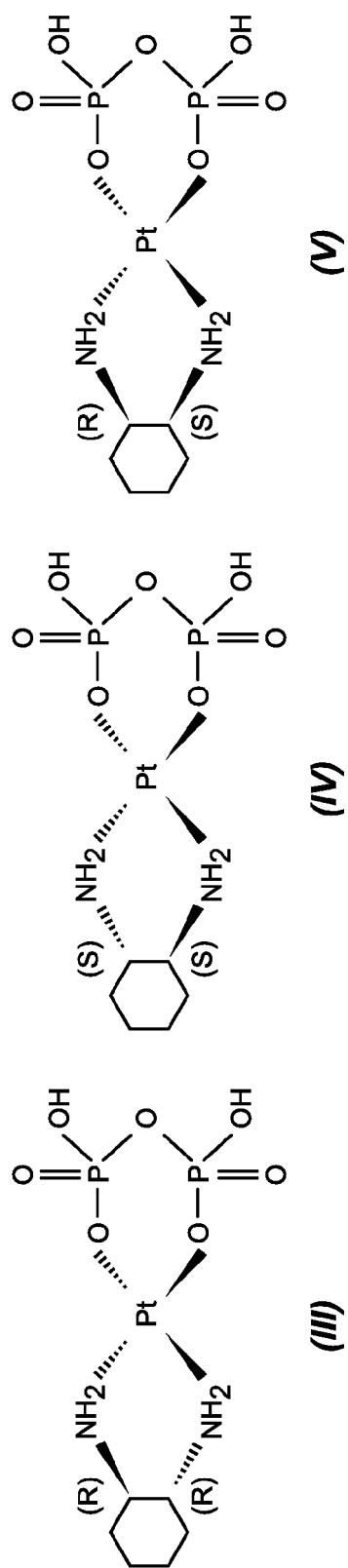
FIG. 2. Shows examples of cis-, trans- and optical isomers of general formula (I) as exemplified in formulas (III) through (V) for platinum (II) complexes and formulas (VI) through (VIII) for platinum (IV) complexes using a chiral amine ligand, 1,2-diamine cyclohexane.
Figure 2:
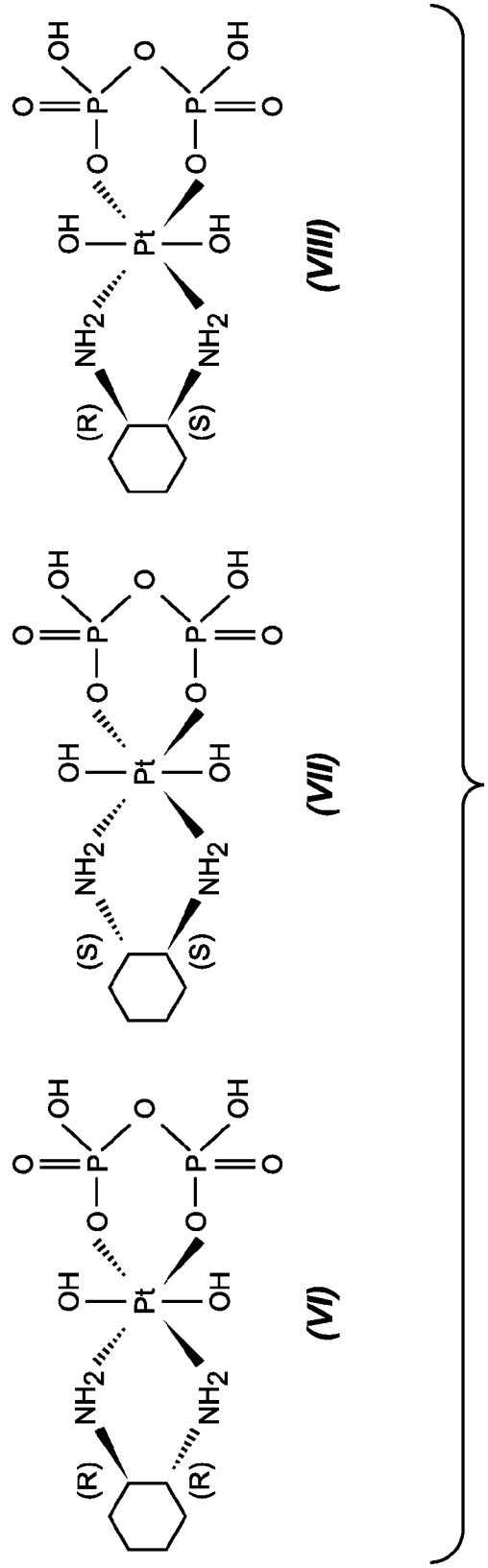

The present invention describes new processes for making large quantities of phosphaplatins that eliminates both large volumes of starting reaction mixtures and alleviates the concentration process for precipitation, and reduces the reaction time. The phosphaplatins of the present invention can be described by general formula (I) depicted in FIG. 1, where R1 and R2 are amine ligands, and R3 and R4 are either amine or other monodentate ligands. Of particular interest are also the many chemical variations of these phosphaplatin structures, which include cis-, trans-, racemic and enantio-pure forms where the amine ligands contain chiral centers. Examples of such cis-, trans- and optical isomers of general formula (I) are shown in FIG. 2 with formulas (III) through (V) for platinum (II) complexes, and formulas (VI) through (VIII) for platinum (IV) complexes using a chiral amine ligand, 1,2-diamine cyclohexane. The processes of the present invention are also applicable to triphosphate and polyphosphate compounds.

Figure 3:
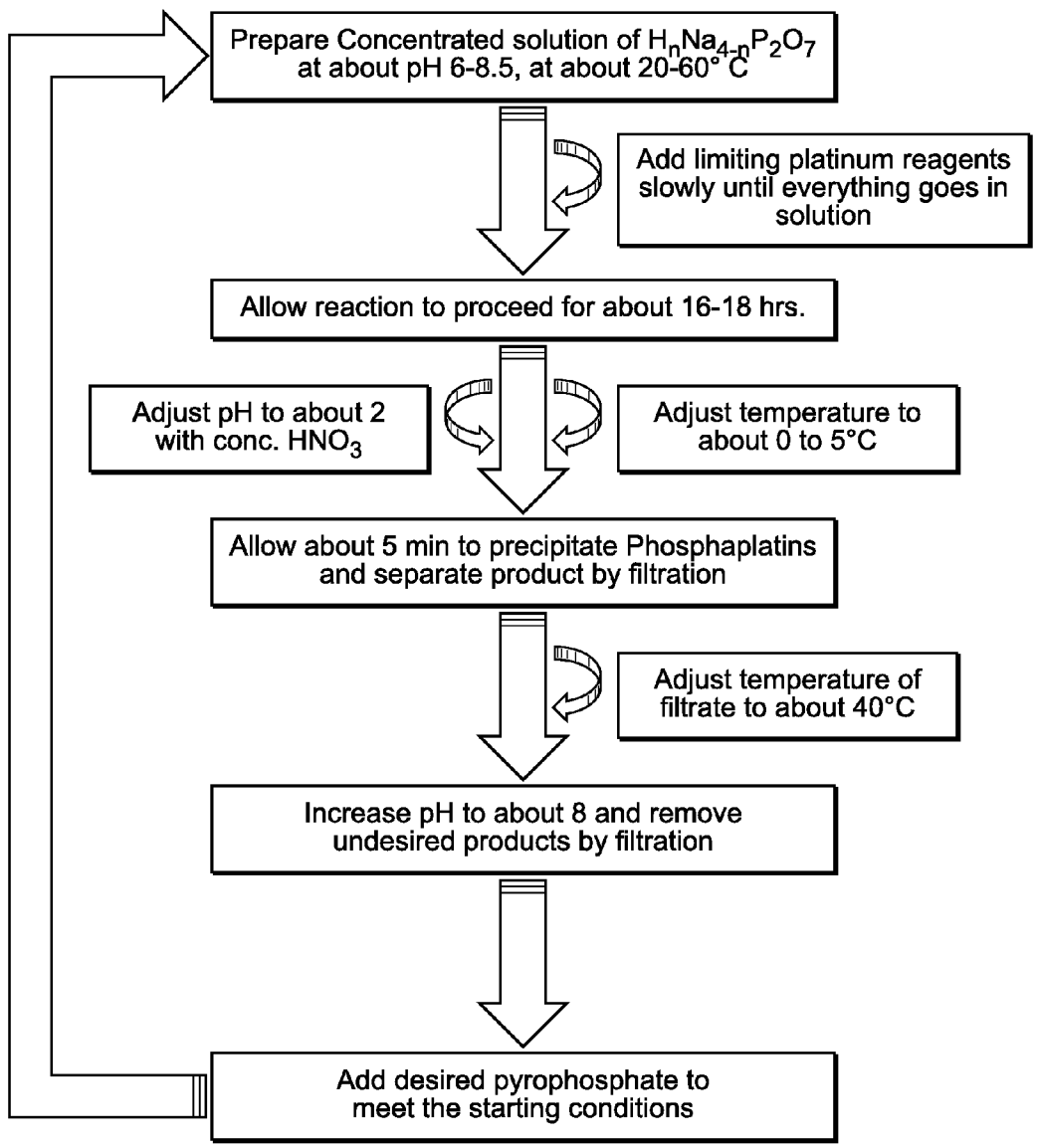
FIG. 3. Shows a schematic representation of large scale production of phosphaplatins.

One embodiment of the present invention is described in FIG. 3 by way of non-limiting example. In this process, platinum reagents of general formula $PtA_2X_2$ (where A is an inert monodentate ligand or $A_2$ is a bidentate ligand, and X is a replaceable ligand) are added to a saturated solution of $H_nNa_{4-n}P_2O_7$ at a pH of between about 6.0 and 8.5, preferably about 8, and at a temperature of between about 20° C. and 60° C., preferably between about 20° C. and 50° C., and more preferably about 40° C. Next, the reaction is stirred for approximately 6-15 hours (depending upon the process conditions previously mentioned since reaction time is reduced at higher temperatures). After stirring, the pH is adjusted with concentrated $HNO_3$, and temperature is adjusted to about 0-5° C. The reaction mixture is left on ice for 5 minutes (depending upon conditions) to precipitate out the phosphaplatins, and then the phosphaplatins are filtered out. The temperature of the filtrate is adjusted to about 40° C. and then let stand for about two hours, preferably a few minutes, to precipitate out dimers and oligomers, if any. Finally, the pH of the filtrate is adjusted to between 6.0 and 8.5, preferably pH 8, appropriate amounts of pyrophosphate and starting platinum reagents are added to meet starting conditions, and the above steps are then repeated to yield further phosphaplatins.

In another embodiment, by way of non-limiting example, a concentrated solution of tetrasodium pyrophosphate (~0.4 g) is prepared in a minimum volume of water at about 40° C. by adjusting the pH with concentrated nitric acid. This limiting minimum volume is equal to the solubility of pyrophosphate at about pH 8 and at about 40° C. The starting platinum compound (~0.1 g) is slowly added to the pyrophosphate solution under vigorous stirring until the platinum compound is completely dissolved in the solution. The reaction mixture is then maintained at about 40° C. for about 12 hr. Typically, this total volume of the reaction mixture in this specific example can be on the order of about 10 mL instead of much larger prior art volumes, such as 250 mL. At the end of the reaction time, aliquots of nitric acid of desired concentration are added to lower the pH to about 2. The concentration and volume of nitric acid depend on the desired adjustment of final volume to precipitate the compound. The final volume is calculated based on the solubility of pyrophosphate moiety at about pH 2 and at about 5° C. so that the excess of un-reacted pyrophosphate does not precipitate out. Upon cooling this solution briefly, the desired phosphaplatin complex precipitates out. Typically, the total volume after the pH adjustment can be brought to about 8-10 mL.

This improved method and process can be applied to all phosphaplatin compounds. The process can be scaled up by increasing the concentration of reactants and adjusting the volumes accordingly. As an example, in one embodiment, one kilogram of a phosphaplatin complex can be synthesized in 10 to 20 L volumes, instead of the much larger five thousand liter volumes described in the prior art.

Another advantage of the disclosed process is its potential to recycle the mother liquor after collecting the first crop of phosphaplatins, which contains unused starting platinum complex and pyrophosphate along with the product that was not precipitated due to its inherent solubility. For example, in one embodiment, after the first crop of phosphaplatins are removed from the mother liquor, the temperature of the mother liquor is increased again to 40° C. and the reaction mixture is let stand for 2 hrs, preferably a few minutes. Undesired products, including dimeric/polymeric pyrophosphate complexes (if any), are then filtered out. In this non-limiting example, additional pyrophosphate is added at a concentration necessary to exceed the amount of platinum reactant for the synthesis via a kinetic controlled process. Since up to 25% of the starting pyrophosphate ligand is consumed in the reaction, 75% of the un-reacted starting pyrophosphate can be reused.

In another embodiment, the first reaction is conducted using ten-fold excess of pyrophosphate ligand. In the subsequent cycle, only the starting platinum complex needs to be replenished until the mole ratio of platinum:pyrophosphate reaches 1:4. At that stage, additional pyrophosphate is added to meet the kinetic criteria and to avoid the formation of dimeric product. In yet another alternative embodiment, a low-volume synthesis of phosphaplatins is obtained by removing the chloride or iodide ligand from the starting platinum complex, thus creating a highly soluble di-aqua-platinum(II) compound, and reacting that compound with the pyrophosphate moiety. Under such conditions, the reaction yields several minor products in addition to the major monomeric phosphaplatin complexes.

The advantages of the processes disclosed herein are many, including but not limited to minimizing the need for use of large volumes of starting reaction mixtures. This is possible because the improved processes disclosed herein take advantage of the large solubility of pyrophosphate moiety in the pH range from 6 to 8.5, which is followed by the addition of the starting platinum complexes until they dissolve. As a result, the entire process disclosed herein is not limited by the poor solubility of the starting platinum complex material (which is a critical limitation to other synthetic methods disclosed in the prior art).

Platinum (IV) complexes were also synthesized following the low-volume strategy by oxidizing the platinum (II) complexes with hydrogen peroxide at the end of the incubation time at pH 6-8 (see Example 6). Hence, the invention is equally applicable to low-volume synthesis of platinum (II) and platinum (IV) complexes.

In addition, the disclosed processes lead to the elimination or minimization of the formation of undesired complexes, including dimeric and oligomeric species, by slowly adding the starting platinum substrates. This slow addition of starting platinum reactants ensures a condition of excess pyrophosphate environment that prevents the formation of undesired dimeric and oligomeric platinum complexes. Furthermore, rapid precipitation in the processes disclosed herein can be accomplished by merely lowering the temperature, and does not require the need for concentrating the reaction mixture. Once the undesired dimeric and oligomeric platinum products are isolated, the leftover, un-reacted pyrophosphate can be reused for the next batch, which can represent up to 75% of the initial quantity. As a result, the overall cost of the process is significantly decreased.

The present invention is useful for the treatment of cancer patients, and other clinical applications. It can also be used in other applications where significant quantities of compounds are desired.

While the invention described herein specifically focuses on a novel process for making large quantities of phosphaplatin compounds, one of ordinary skills in the art, with the benefit of this disclosure, would recognize the extension of such approaches to other systems. It will be appreciated by those skilled in the art that changes could be made to the embodiments described above without departing from the broad inventive concept thereof. It is understood, therefore, that the invention disclosed herein is not limited to the particular embodiments disclosed, but it is intended to cover modifications within the spirit and scope of the present invention as defined by the appended claims.

EXAMPLES

Example 1

Low-Volume Synthesis of (trans-1,2-Cyclohexanediamine)(dihydrogen pyrophosphato)platinum (II) (trans-dach-2) or (1R,2R-cylohexanediamine)dihydrogen-pyrophosphato-platinum(II) (RR-dach-2)

Figure 4A:
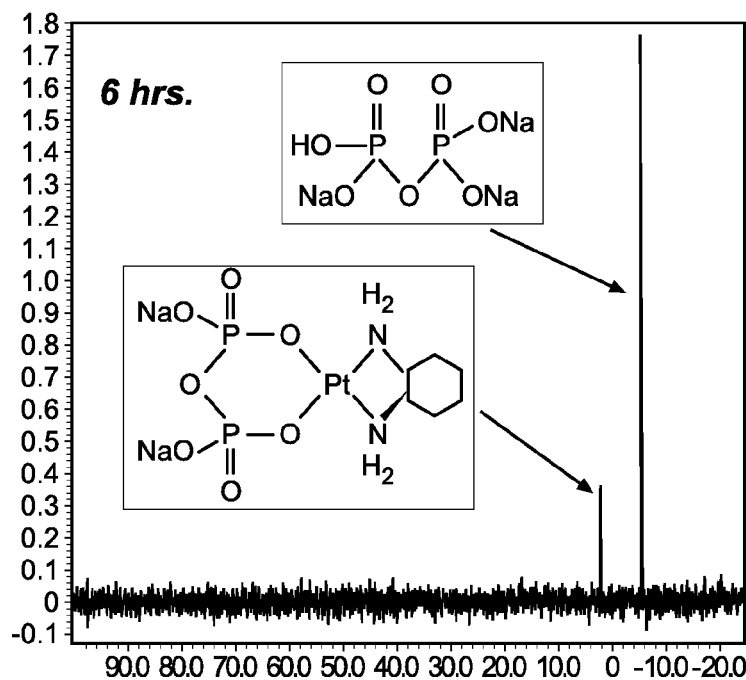
FIGS. 4A-4C. Show a Phosphorous-31 NMR spectrum of a reaction mixture produced from an embodiment of the present invention.
Figure 4B:
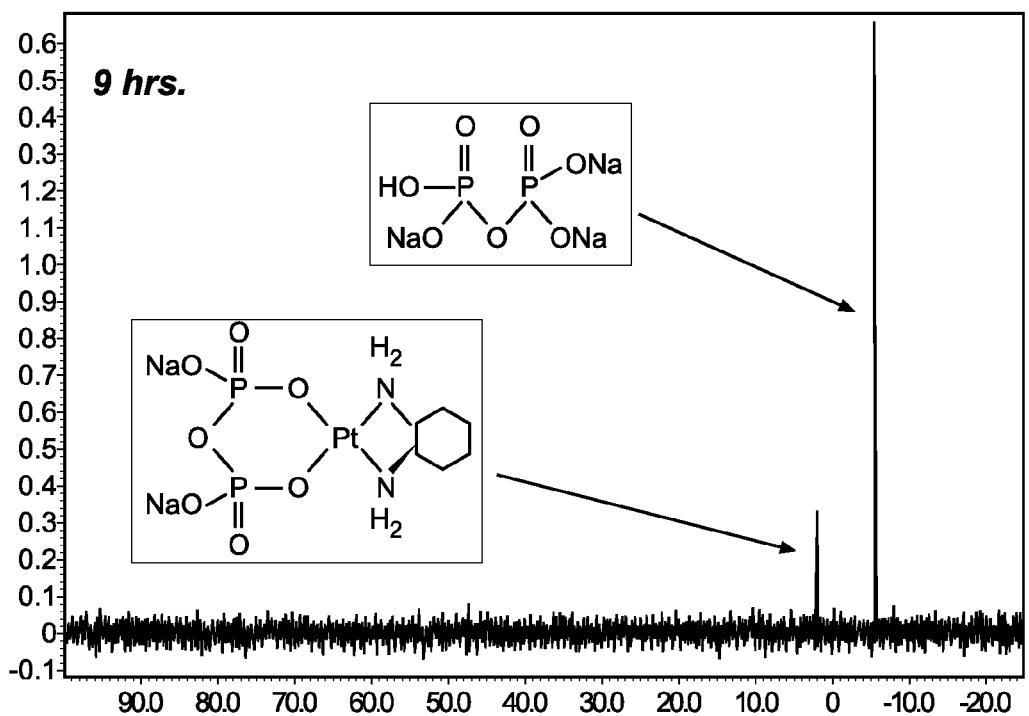
Figure 4C:
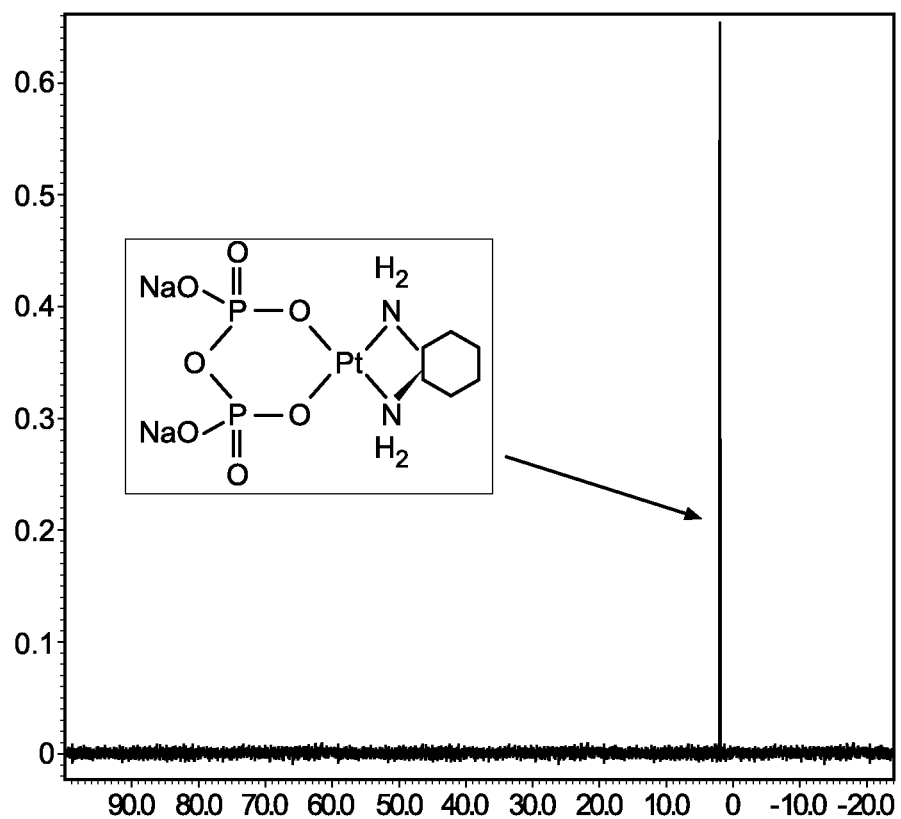

Sodium pyrophosphate decahydrate (0.4 g) was dissolved in 25 mL of distilled water at 60° C. and the pH of the solution was adjusted to 8 with 1M $HNO_3$. The solution was kept at 60° C. for 15 minutes and then 0.1 g of cis-dichloro(trans-1,2-cyclohexanediamine)platinum(II) or cis-dichloro-(trans-1R,2R-cyclohexanediamine)platinum(II)) was added in small quantities over a 30 min period. The reaction mixture was incubated at 60° C. for 15 hours mixing time. FIGS. 4A-4C show one example of phosphorus-31 NMR spectra of the reaction mixture recorded after 6 and 9 hr of reaction at 60° C., and the final product isolated from the reaction. The downfield peak at 1.93 ppm is for the monomeric pyrophosphate complex, and the peak at −5.62 is for the excess unreacted pyrophosphate ligand. As seen in the Figures, there is no change in relative intensity of the product peak after 6 hrs of reaction time indicating that the reaction time can be shortened considerably. In fact, prolonged reaction times beyond 9 hr at 60° C. seemed to reduce the product peak. Furthermore, it is possible to reduce the reaction time by increasing the temperature below the decomposition of the pyrophosphate ligand. Following the incubation period, the solution was filtered to remove any un-reacted starting material and was concentrated to 5-7 mL by rotary evaporation under vacuum at 48° C. The pH was lowered to approximately 1.5-2 by the addition of 1 N $HNO_3$, and temperature was lowered to 4° C. to precipitate out the product as a light-yellow powder. Precipitation was completed by cooling on ice for 5 minutes, and the product was isolated by vacuum filtration and washed with ice cold water and acetone (three times at 10 mL per wash). The final product was dried under vacuum in a desiccator overnight. Yields of $[Pt(C_6H_{14}N_2)(H_2P_2O_7)]$ were in the range of 0.06 g. The average percent yield was 50%. The volume of the starting reaction mixture can be lowered further to 7-10 mL to eliminate the concentration step. However, the product yield is significantly reduced. As discussed in further detail below, the product obtained was fully characterized by Pt elemental analysis, P-31 NMR spectroscopy, HPLC, and mass spectrometry.

The reaction was repeated under identical conditions by lowering the temperature at 40° C. The same product featuring identical analytical characteristics stated above was obtained. The only difference is that the reaction time was extended.

Example 2

HPLC Characterization

Figure 5A:
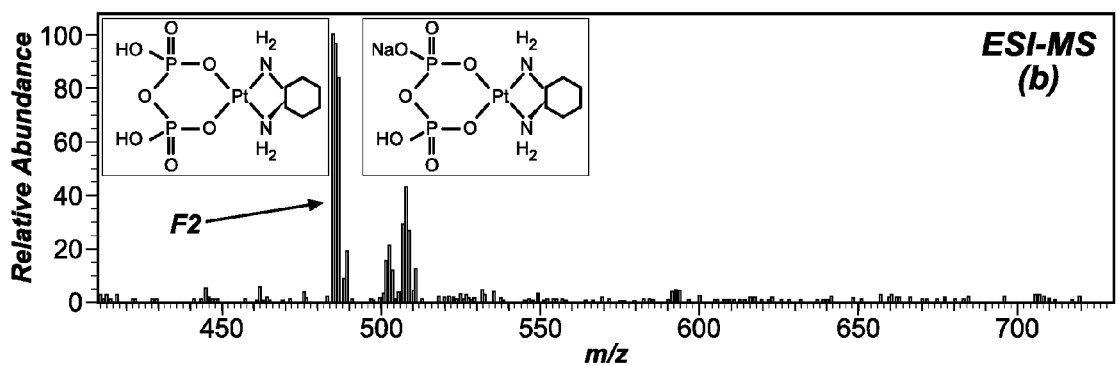
FIGS. 5A-5C. Show HPLC data for products recovered after performing a process according to an embodiment of the present invention.
Figure 5B:
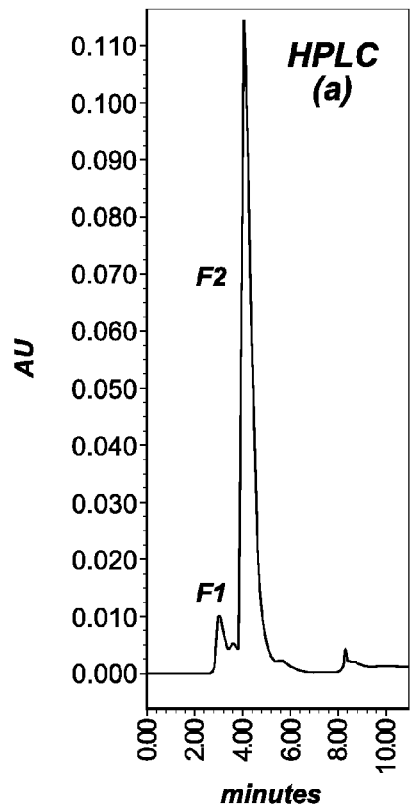

FIG. 5B shows a high performance liquid chromatogram of the products recovered after the above first reaction cycle recorded immediately after dissolving the product (1 mg) in 600 μL of 25 mM sodium bicarbonate at pH 7.5. A 50 μL aliquot of the sample was injected for the separation. Each separation was repeated three times. The high performance liquid chromatography experiments were performed on a Waters HPLC system equipped with a dual gradient programmer and a photodiode array detector (Waters). Gradient separations were performed on a C18 column (Waters, XTerra R18, 4.6×150 mm column, 5 micron) by using a mobile phase consisting of 10 mM ammonium acetate (pH 5.5) buffer (solvent A) and acetonitrile (solvent B). The gradient separation consists of linear increase of solvent B from 0% to 30% for the first 30 min followed by a steeper increase of 30 to 100% of B in the next 5 min. Finally, an additional 5 min of isocratic separation was set to 100% A. The flow rate was set at 0.5 ml/min throughout the gradient at room temperature. The respective peaks were collected at the beginning of each eluting peak to the end. Referring to FIG. 2B, the HPLC peaks at 3.04 and 4.2 min correspond to the deligated pyrophosphate ligand and the desired monomeric complex (phosphaplatin), respectively. It is understood that the released ligand and the dimeric compound are formed due to dynamic behavior of the compound in acidic solution, which is absent at neutral pH where only the monomeric compound exists in solution.

Example 3

Mass Spectrometry Characterization

The mass spectrometric analysis of final product and collected HPLC fractions of the final product were performed on LCQ DECA-XP (Thermo-Finnigans) mass spectrometer by direct infusion using 500 μL syringe (2.30 mm diameter) at a 8 μL/min flow rate (infused volume 32 μL). The mass spectrometer was set to positive ion polarity (+MS), dry temperature of 350° C., capillary voltage 30.22 V, sheath gas flow rate at 49.36 l/min, dry gas 5.00 l/min, and tube lens voltage 15.0 V. The mass to charge ratios were collected from 150 to 2000. The collected fractions were also identified via mass spectrometry. Referring to FIG. 5A, the peak at m/z 486.4 corresponds to the desired monomeric complex (phosphaplatin). The peak at m/z 508.1 corresponds to its sodium adduct.

Example 4

NMR Characterization

Figure 5C:
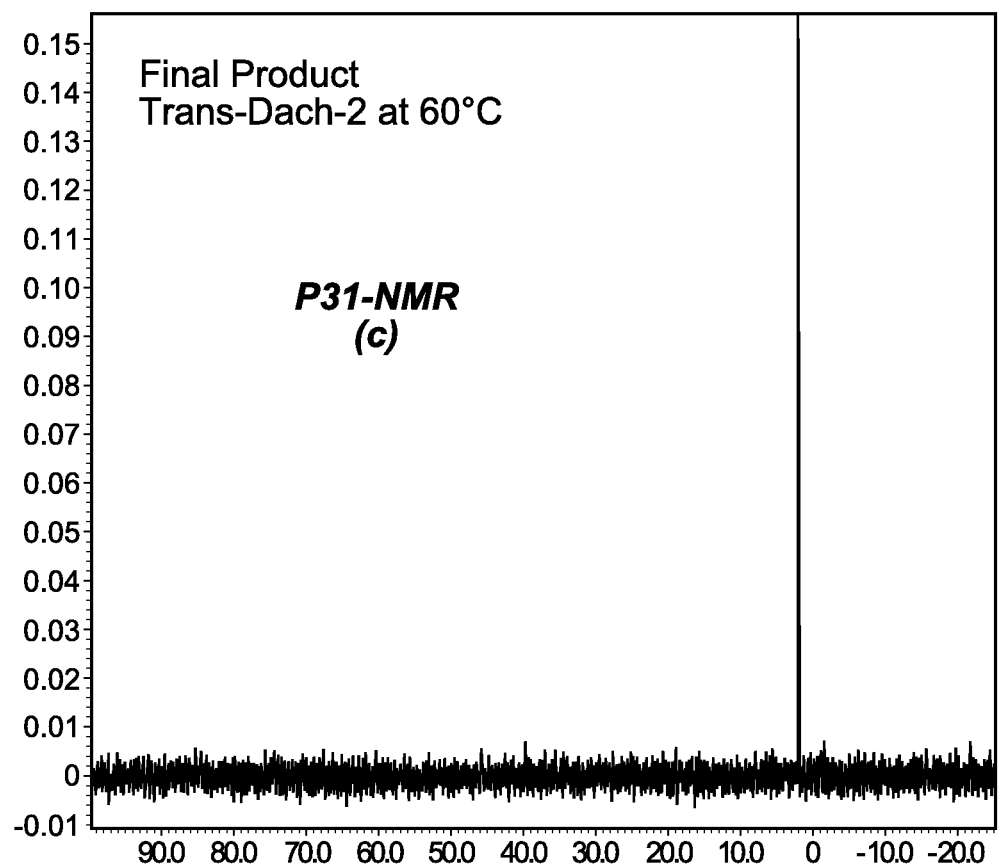

NMR experiments were performed on a JEOL ECA-500 MHz instrument equipped auto-tune broadband n-15-P31 probe using the JEOL delta operation's software. Proton decoupled P-31 resonances were recorded at 202 MHz and their chemical shifts are reported with respect to 85% phosphoric acid at 0.0 ppm. A pulse of 4.6-microsecond with a repetition time of 0.8 s was used to generate Fourier induction decay. Typically, 52 K data points were collected within 31.72 KHz frequency domain. A line-broadening factor of 1.0 Hz was introduced before Fourier Transformation. As shown in FIG. 5C, at pH 7.09, the P-31 NMR spectrum displayed a single peak at 2.02 ppm (trans-dach-2). The product exhibited a single P-31 NMR resonance at 2.02 ppm. Furthermore, when analyzed at pH 7.5, the P-31 NMR spectrum displayed a single peak at 1.92 ppm (RR-dach-2).

Example 5

Recycling the Un-Reacted Materials from Leftover Mother Liquor

The mother liquor left over from the isolation of the product in Example 1 above was used for a second cycle of synthesis by replenishing 0.1 g pyrophosphate ligand along with the 0.1 g of the starting platinum complex. The exact same process explained in Example 1 was followed to isolate the product. The yield of the product again was consistent with the first crop as noted above. The HPLC chromatogram, mass spectra, and P-31 NMR of the product isolated in Example 2 resemble that of the product isolated in Example 1.

Example 6

Low-Volume Synthesis of (trans-1,2-Cyclohexanediamine)-trans-dihydroxo(dihydrogen pyrophosphato)platinum(IV)

Sodium pyrophosphate decahydrate (0.4 g) was dissolved in 25 mL of distilled water at 60° C. and the pH of solution was adjusted to 8 with 1M $HNO_3$. The solution was left at 60° C. for 15 minutes and 0.1 g of the precursor compounds (i.e. cis-dichloro(trans-1,2-cyclohexanediamine)platinum(II) was added in small quantities in a 30 min period. The mixture was incubated at 60° C. for 12 hours. One milliliter of 30% hydrogen peroxide was added to the mother liquor and incubated for another 2 hours at 60° C. Following the incubation period, the solution was filtered to remove any unreacted starting material and was concentrated to 5-7 mL by rotary evaporation under vacuum at 48° C. Lowering the pH to approximately 1.5-2 by the addition of 1 N $HNO_3$ and reducing the temperature to 4° C., a light-yellow powder precipitated out. Precipitation was completed by cooling on ice for 5 minutes, and the product was isolated by vacuum filtration and washed with ice cold water and acetone, thrice at 10 mL per wash. Final product was dried under vacuum in a desiccator for 12 hour. The yield was 0.048 g (35%). The $^{31}P$ NMR spectrum recorded at pH 7.75 exhibited a peak at 2.59 ppm with two satellites at 24.2 Hz apart. HPLC chromatogram of the isolated product (1 mg dissolved in 600 μL of 25 mM sodium bicarbonate at pH 7.5) showed a single peak at 3.63 min which was eluted with a gradient mobile phase consisting of 10 mM ammonium acetate (pH 5.5) buffer (solvent A) and acetonitrile (solvent B) on a C18 column (Waters, XTerra R18, 4.6×150 mm column, 5 micron) as described in Example 2.

What is claimed is:

1. A process for synthesizing phosphaplatins, comprising: concentrating pyrophosphate ligand in a reaction mixture having a pH at approximately 6 to 8.5; and adding platinum complex to the reaction mixture.

2. The process according to claim 1, wherein the reaction mixture is maintained at a temperature between approximately 20° C. to 60° C.

3. The process according to claim 1, wherein the reaction mixture is maintained at a temperature between approximately 20° C. to 50° C.

4. The process according to claim 1, wherein the reaction mixture comprises $H_nNa_{4-n}P_2O_7$.

5. The process according to claim 1, wherein the phosphaplatins are one or any combination of phosphaplatins having the general formula (I),

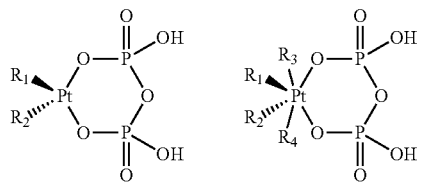

wherein R1 and R2 are amine ligands, and R3 and R4 are either amine or other monodentate ligands.

6. The process according to claim 5, wherein the phosphaplatins include cis-, trans-, racemic and enantio-pure forms.

7. The process according to claim 1, further comprising slowly adding platinum complex to the concentrated pyrophosphate solution at a rate that ensures all of the platinum complex is dissolved into the reaction mixture.

8. The process of claim 7, further comprising stirring the reaction mixture for about 6 to 15 hours after the addition of platinum complex.

9. The process of claim 8, further comprising precipitating out the phosphaplatins by lowering the pH of the reaction mixture to approximately 2, and reducing the temperature to approximately 0-5° C.

10. The process of claim 9, further comprising precipitating out dimers and oligomer byproducts by raising the temperature to approximately 4° C.

11. The process of claim 1, further comprising using unreacted pyrophosphate ligand and platinum complex in a subsequent phosphaplatins synthesis.

12. A process for synthesizing phosphaplatins, comprising:

providing a saturated pyrophosphate solution in a reaction mixture having a temperature between approximately 20° C. and 60° C.;

slowly adding to the reaction mixture platinum complex having the formula $PtA_2X_2$, wherein A is an inert monodentate ligand or $A_2$ is a bidentate ligand, and X is a replaceable ligand;

stirring the reaction mixture; and precipitating out the phosphaplatins by lowering the pH of the reaction mixture to approximately 2, and reducing the temperature to approximately 0-5° C., wherein the synthesized phosphaplatins have the formula:

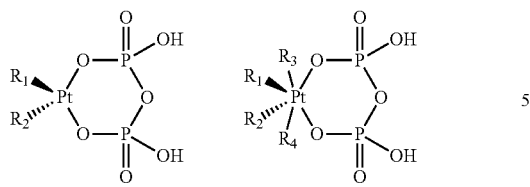

wherein R1 and R2 are amine ligands, and R3 and R4 are either amine or other monodentate ligands.

13. The process according to claim 12, wherein the reaction mixture is maintained at a temperature between approximately 20° C. to 50° C.

14. The process according to claim 12, wherein reaction mixture comprises $H_nNa_{4-n}P_2O_7$.

15. The process according to claim 12, wherein the phosphaplatins include cis-, trans-, racemic and enantio-pure forms.

16. The process of claim 12, further comprising stirring the reaction mixture for about to 15 hours after the addition of platinum complex.

17. The process of claim 12, further comprising precipitating out dimers and oligomer byproducts by raising the temperature to approximately 40° C.

18. The process of claim 12, further comprising using un-reacted pyrophosphate ligand and platinum complex in a subsequent phosphaplatins synthesis.

19. A process for synthesizing phosphaplatins, comprising: concentrating pyrophosphate ligand in a reaction mixture comprising $H_nNa_{4-n}P_2O_7$; and adding platinum complex to the reaction mixture.

\* \* \* \* \*